United States Patent [19]
Cowan

[11] Patent Number: 5,911,166
[45] Date of Patent: Jun. 8, 1999

[54] TENSILE STRENGTH TESTER WITH CLAMPING LOAD APPLICATION CONTROL

[76] Inventor: Wavell F. Cowan, HCR 34 Box 45, Montpelier, Vt. 05602

[21] Appl. No.: 08/922,316

[22] Filed: Sep. 3, 1997

[51] Int. Cl.⁶ ..................................................... G01N 3/04
[52] U.S. Cl. ................................................ 73/833; 73/831
[58] Field of Search ............................. 73/826, 831, 833, 73/834, 835, 838, 840

[56] References Cited

U.S. PATENT DOCUMENTS

| | | | |
|---|---|---|---|
| 2,849,048 | 8/1958 | Curtner | 73/826 |
| 2,886,967 | 5/1959 | Conti | 73/836 |
| 3,620,071 | 11/1971 | Kelly et al. | 73/826 |
| 3,707,119 | 12/1972 | Cowan | 73/837 |
| 4,059,992 | 11/1977 | Cowan et al. | 73/837 |
| 5,437,192 | 8/1995 | Kawamoto et al. | 73/831 |
| 5,581,040 | 12/1996 | Lin | 73/833 |

*Primary Examiner*—Max H. Noori
*Attorney, Agent, or Firm*—Diller, Ramik & Wight, PC

[57] ABSTRACT

A testing apparatus for measuring the tensile strength of a flat sheet of material with a set of clamping jaw members having respective clamping surfaces. A cylinder is provided for closing the first and second jaw members in a clamped position. Transitional members are provided for transferring the load developed by the cylinder to the first and second jaw members without any bending deflections occurring at the clamping surfaces which secure the sheet sample.

20 Claims, 5 Drawing Sheets

TENSILE STRENGTH TESTER WITH CLAMPING LOAD APPLICATION CONTROL

BACKGROUND OF THE INVENTION

1. Field of the Invention

The present invention relates to an apparatus for testing the tensile strength of sheet material and, more particularly, to an improved clamping jaw assembly which is adapted to transfer compression forces directly to the sheet material to be tested.

2. Description of the Prior Art

U.S. Pat. Nos. 3,707,119, issued Dec. 26, 1972, and 4,059,992, issued on Nov. 29, 1977, to Wavell F. Cowan, disclose testing devices for measuring the tensile strength of sheet material, such as paper. Basically, these testing devices comprise pairs of opposite clamping jaws which are respectively adapted to clamp a portion of the sheet material adjacent to the portion clamped by the opposed pair of clamping jaws. One of the opposed pairs of clamping jaws is adapted to move away from the other between a first position whereby the two pairs of opposite clamping jaws are juxtaposed in contact with each other and a position spaced apart from each other with the clamping jaw still gripping portions of the sheet. Means are provided for pivotally causing the movement of one pair of clamping jaws relative to the other.

Each pair of clamping jaws of the testing device described in U.S. Pat. 4,059,992 is provided with a fixed jaw member and a moveable jaw member. Low pressure, large diameter, pneumatic cylinders are provided for moving the moveable jaw members towards the fixed jaw members against a self-aligning cylindrical spring of each pair of clamping jaws.

Although the testing devices described in the above-mentioned patents are very effective, it has been found that some deflection still affects the uniformity of the clamping surfaces of the fixed and the moveable jaw members. Indeed, according to these constructions, some bending forces are induced in the moveable jaw members. In some applications, eliminating even very small deflection at the clamping surfaces is hugely beneficial to the accuracy of the tensile test.

SUMMARY OF THE INVENTION

It is, therefore, an aim of the present invention to provide a tensile strength tester which is adapted to accurately measure the tensile strength of sheet material.

It is also an aim of the present invention to provide such an apparatus which is adapted to ensure that no bending stress is induced in the jaw members used to clamp the flat sheet to be tested.

A construction in accordance with the present invention for testing the tensile strength of fibers in a flat sheet comprises a base structure and a stationary clamping jaw assembly mounted to the base structure and adapted to clamp a sheet of material to be tested. The testing apparatus further comprises a moveable clamping jaw assembly mounted to the base structure opposite to the stationary clamping jaw assembly for clamping the sheet material adjacent to the stationary clamping jaw assembly. The moveable clamping jaw assembly is displaceable along a longitudinal axis passing through the center of the stationary clamping jaw assembly.

Each stationary and moveable clamping jaw assembly includes first and second jaw members which are provided with respective clamping surfaces to receive and clamp the sheet of material at adjacent points of contact. Each stationary and moveable clamping jaw assembly further includes pressure means to apply a load for closing the first and second jaw members in a clamped position. A load concentrating means is associated with each pressure means. Each load concentrating means is in contact with at least one of the first and second jaw members at a location which is intersected by an axis which is perpendicular to the clamping surfaces in the clamped position and which passes through the clamping surfaces at the points of contact with the flat sheet of paper for transferring the load to the first and second jaw members along that axis, thereby providing direct compression force at the clamping surfaces.

Motive means are provided for moving the moveable clamping jaw assembly towards and away from the stationary clamping jaw assembly. More particularly, the moveable clamping jaw assembly is displaced by the motive means along the longitudinal axis passing through the center of the stationary clamping jaw assembly. The motive means is connected to the moveable clamping jaw assembly so as to apply a force along the clamped surfaces of the first and second jaw members in the clamped position thereof, thereby exerting a tensile force in the sheet of material clamped by the moveable and stationary clamping jaw assemblies.

Typically, the stationary clamping jaw assembly is secured to the base structure by way of a bracket means. The bracket means is adapted to provide a reaction force which has the same magnitude and line of action as the force applied by the motive means.

Also typically, an alignment means is provided to ensure that the moveable clamping jaw assembly is aligned with the stationary clamping jaw assembly. In accordance with a general aspect of the present invention, the alignment means is provided on each side of the stationary and moveable clamping jaw assemblies. Furthermore, the alignment means includes a side plate fixedly mounted to the base structure and a pair of alignment pads disposed on opposite sides of the stationary and moveable clamping jaw assemblies. Each alignment pad is connected to a pair of fluid operated cylinders to press the stationary and moveable clamping jaw assemblies against the side plate. It is noted that the side plate and the alignment pads are made of frictionless material.

In accordance with a general aspect of the present invention, each stationary and moveable clamping jaw assembly includes biasing means for urging the first jaw member thereof to an open position when the load exerted by the pressure means is released.

Typically, the first jaw member is pivotally mounted to the second jaw member. Each biasing means may comprise a spring mounted on a rod which extends through a hole defined in the first jaw member. The rod may be secured at one end thereof to the second jaw member and provided at opposite ends thereof with nut means to hold the spring against the first jaw member such that, when the first jaw member is moved against the second jaw member, the spring is under compression.

In a more specific construction in accordance with the present invention, the stationary and moveable clamping jaw assemblies include pivot means disposed between the first and second jaw members for directing the motion of the first jaw member relative to the second jaw member.

Each load concentrating means may be in contact with at least one of the first and second jaw members at a second location which is intersected by an axis which is perpendicular to the clamping surfaces in the clamped position and which passes through a center point of the pivot means for transferring the load to the first and second jaw members into direct compression forces, thereby preventing deflections from effecting the uniformity of the clamping surfaces.

More specifically, each load concentrating means includes first and second load bars which are respectively pivotally mounted at the second location on a surface of the first and second jaw members opposite to the clamping surfaces thereof. The first and second load bars are provided with respective load application portions which respectively protrude from the first and second load bars towards the first and second jaw members at the locations which are intersected by an axis which is perpendicular to the clamping surfaces in the clamped position and which passes through the clamping surfaces at the points of contact with the flat sheet of paper for transferring the load developed by the pressure means to the first and second jaw members into direct compression forces.

Typically, each pressure means is a fluid operated cylinder mounted on the first load bar associated therewith. Each cylinder is provided with a piston rod which is adapted to extend and move within a passage defined in the first load bar and in the first and second jaw members. The piston rod is pivotally connected to a rod which is in turn pivotally connected to the second load bar such that, when activated, the cylinder will act to pull the first and second load bars together, thereby causing the pivotal movement of the first jaw member towards the second jaw member so as to close the first and second jaw members in the clamped position thereof.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF THE PREFERRED EMBODIMENTS

Figure 1:
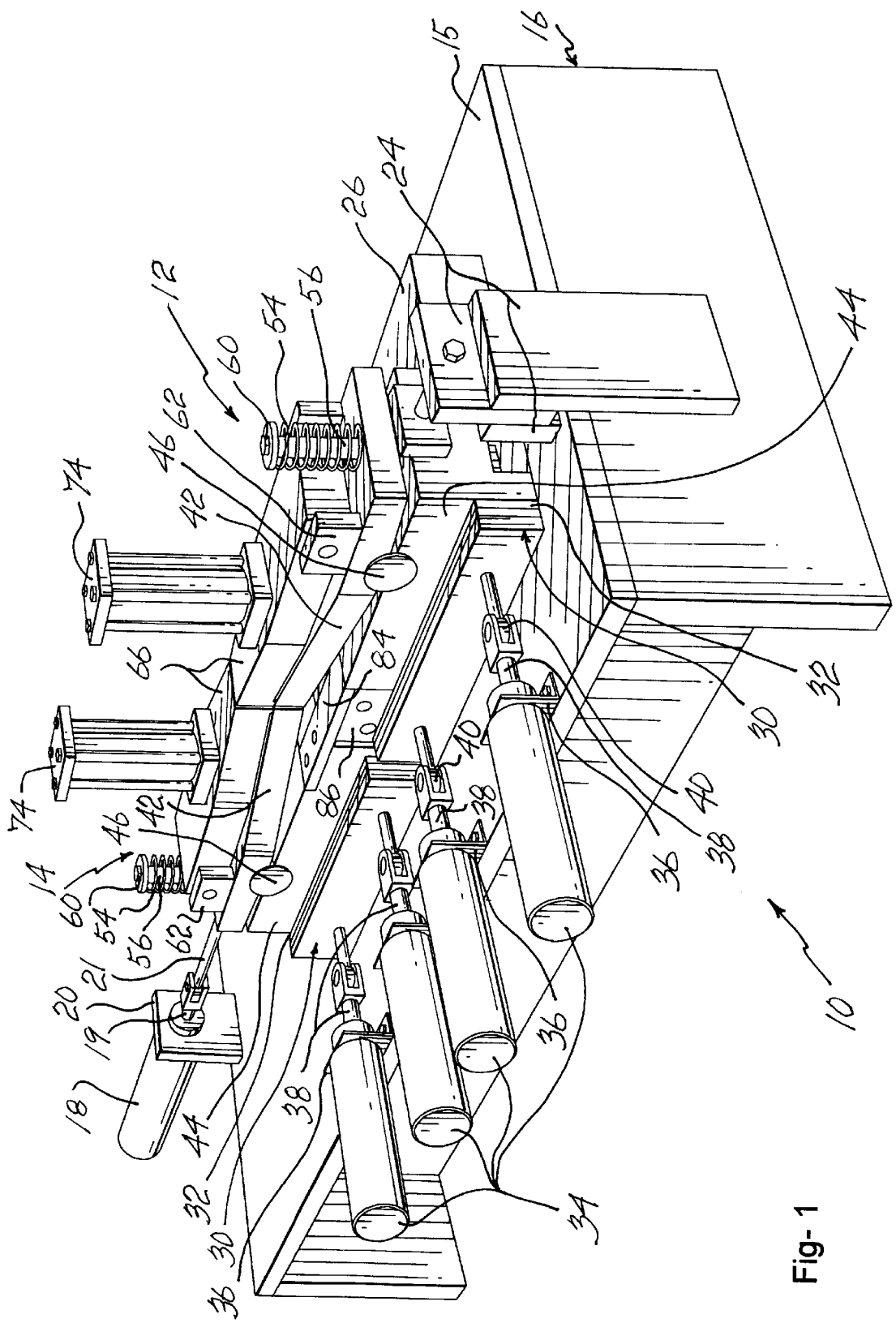
FIG. 1 is a perspective view of the apparatus in accordance with the present invention.
Figure 2:
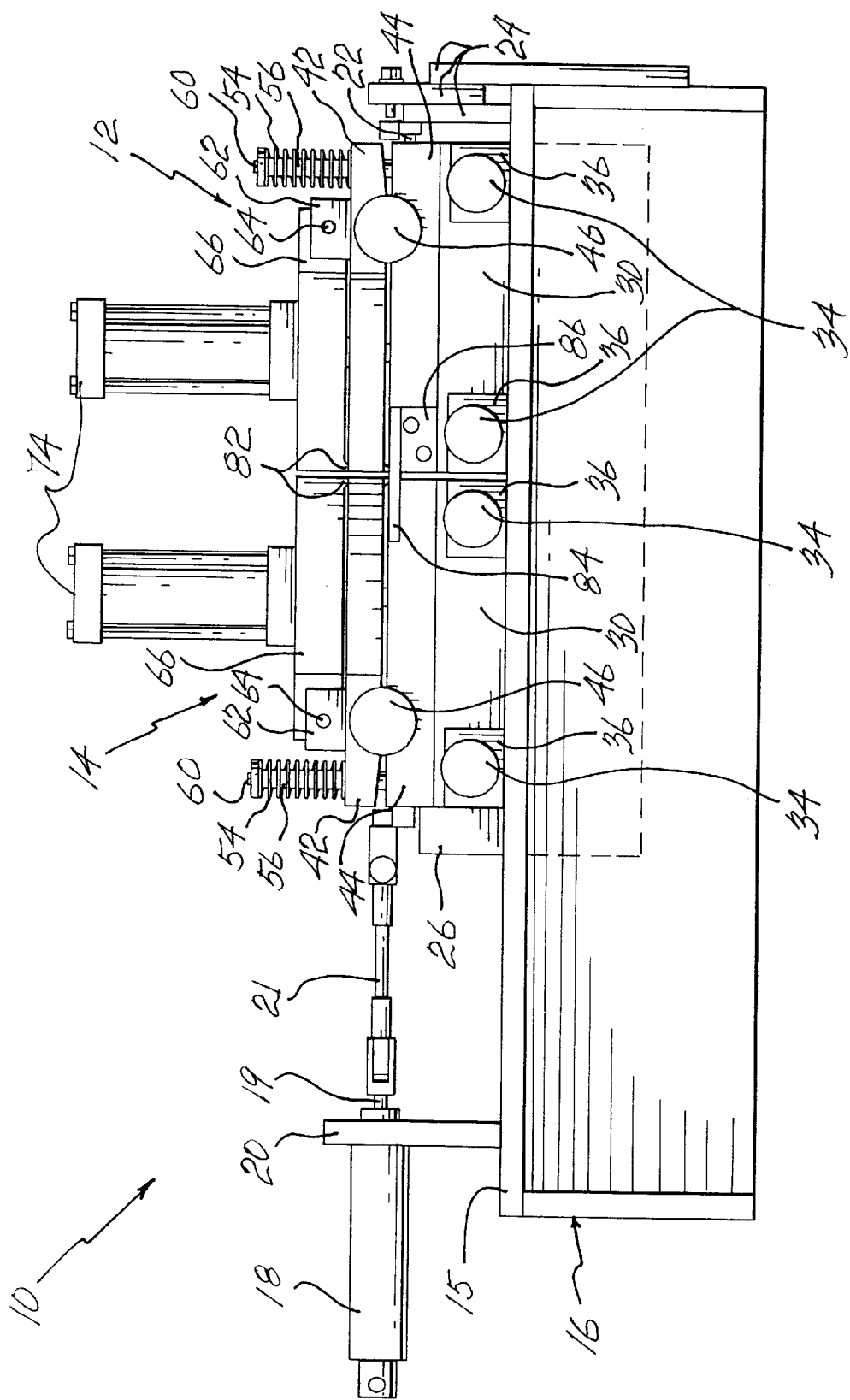
FIG. 2 is a side elevation view of the apparatus of the present invention in a clamped position thereof.

Referring now to the drawings, and in particular to FIG. 1, an apparatus for testing the tensile strength of sheet material, such as paper, embodying the elements of the present invention and generally designated by the numeral 10, will be described.

More specifically, a set of opposed clamping jaw assemblies, including a stationary clamping jaw assembly 12 and a moveable clamping jaw assembly 14, are disposed on a granite base plate 15 of a base structure 16 for respectively receiving and clamping a portion of a sheet material adjacent to the portion clamped by the opposed clamping jaw assembly. A fluid operated cylinder 18 mounted on the base structure 16 by means of a mounting bracket 20 is adapted to displace the moveable clamping jaw assembly 14 towards and away from the stationary clamping jaw assembly 12. More particularly, the moveable clamping jaw assembly 14 is displaceable on the granite base plate 15 along a longitudinal axis which passes through the center of the stationary clamping jaw assembly 12.

Figure 3:
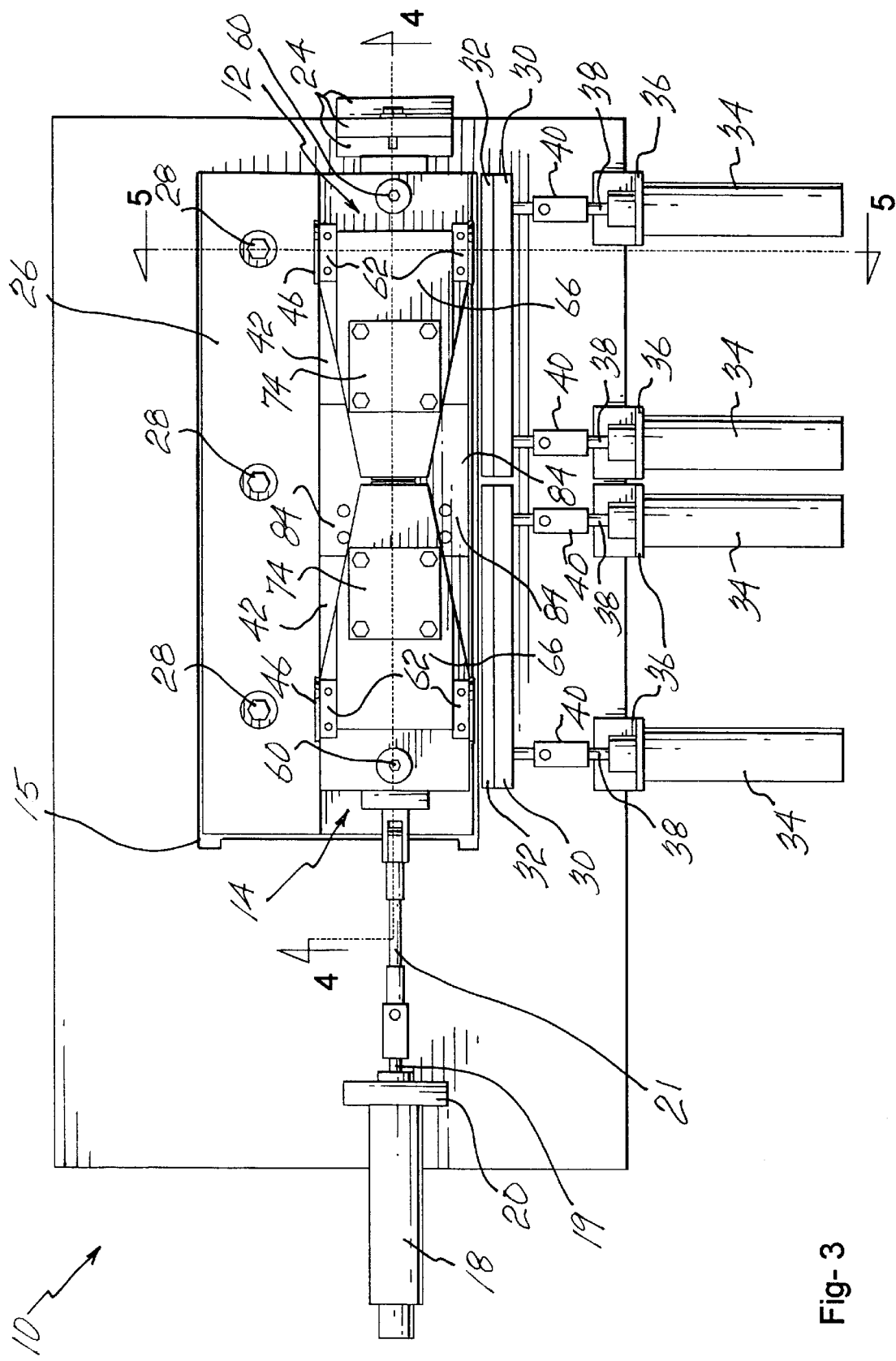
FIG. 3 is a top plan view thereof.

As best seen in FIG. 3, the piston rod 19 of the fluid operated cylinder 18 is pivotally mounted along a horizontal plane to a rod 21 which is in turn pivotally mounted in a vertical plane to the moveable clamping jaw assembly 14. At the opposite end, the stationary clamping jaw assembly 12 is held in a stationary position by a cap screw 22 connected via a back support plates arrangement 24 to the base structure 16. The cylinder 18 and the bracket means, namely the cap screw 22 and the back support plates arrangement 24, are respectively connected to the moveable and stationary clamping jaw assemblies 14 and 12 so as to exert tensile and reaction forces along the plane of the clamped sheet material. Accordingly, when activated, the fluid operated cylinder 18 will pull the moveable clamping jaw assembly 14 away from the stationary clamping jaw assembly 12, thereby exerting a tensile load in the sheet material clamped by both clamping jaw assemblies.

Figures 5, 6:
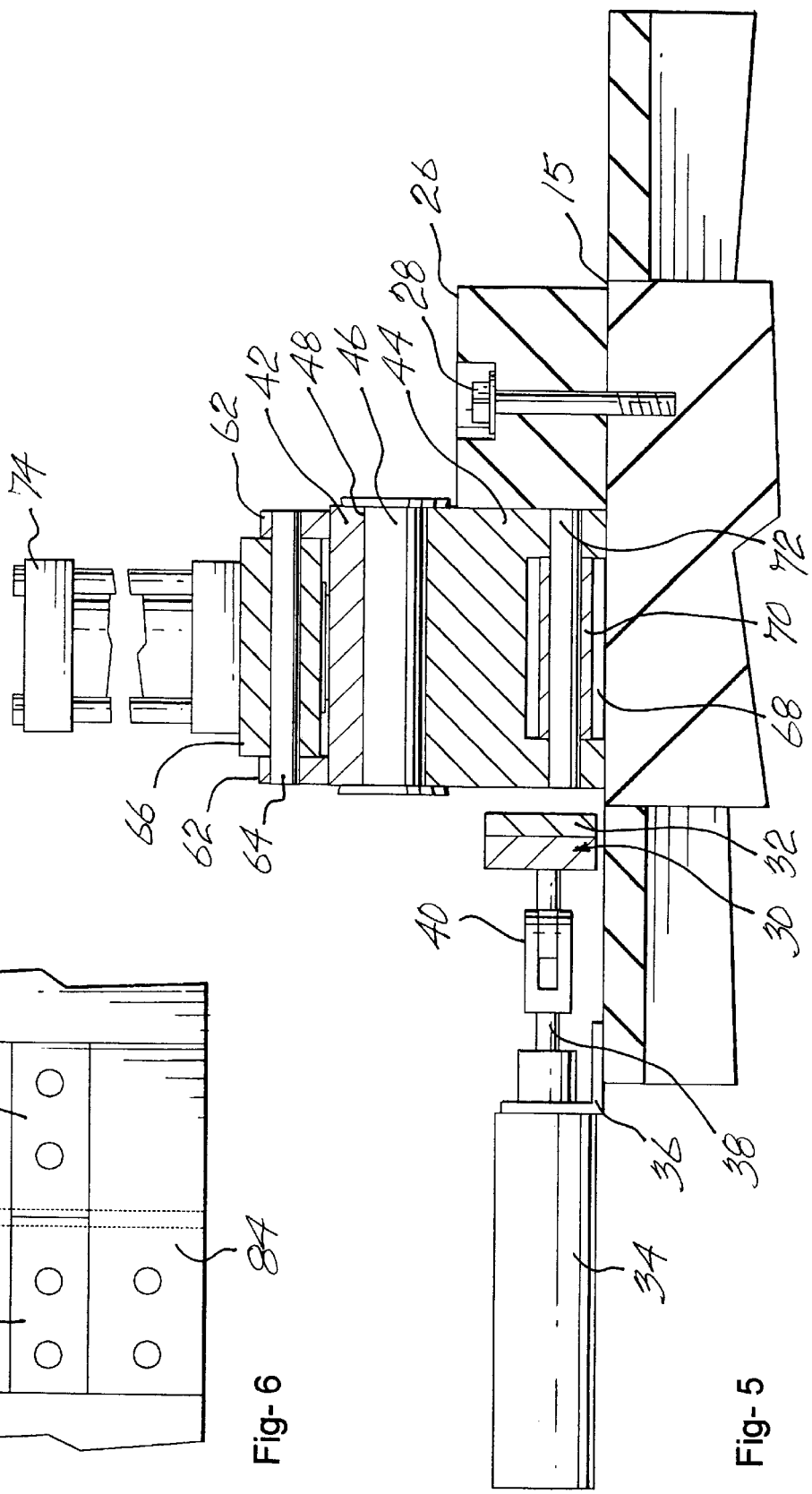
FIG. 5 is a cross-sectional view taken along line 5—5 of FIG. 3.
FIG. 6 is a fragmentary top plan view of the clamping surfaces of the bottom jaw members.

As best seen in FIGS. 1, 3, and 5, the stationary and moveable clamping jaw assemblies 12 and 14 are properly aligned with respect to each other by a granite side plate 26 fixedly mounted to the granite base plate 15 of the base structure 16 by way of bolts 28. A pair of alignment pads 30 faced with Teflon material 32 and disposed on the opposite side of the bottom portion of the stationary and moveable clamping jaw assemblies 12 and 14, for pressing the clamping jaw assemblies 12 and 14 against the granite side plate 26 upon activation of the air cylinders 34 associated with both alignment pads 30. Each alignment pad 30 is connected to a pair of air cylinders 34. Each air cylinder 34 is mounted to the granite base plate 15 of the base structure 16 by means of a mounting bracket 36. The piston rod 38 of each air cylinder 34 is provided with a hinge connection member 40 which is in turn secured to one of the alignment pads 30. Thus the alignment pads 30 are able to slightly pivot in the plan of the granite base plate 15 for facilitating the adjustments which could be required to ensure that the stationary and moveable clamping jaw assemblies 12 and 14 are perfectly aligned.

Figure 4:
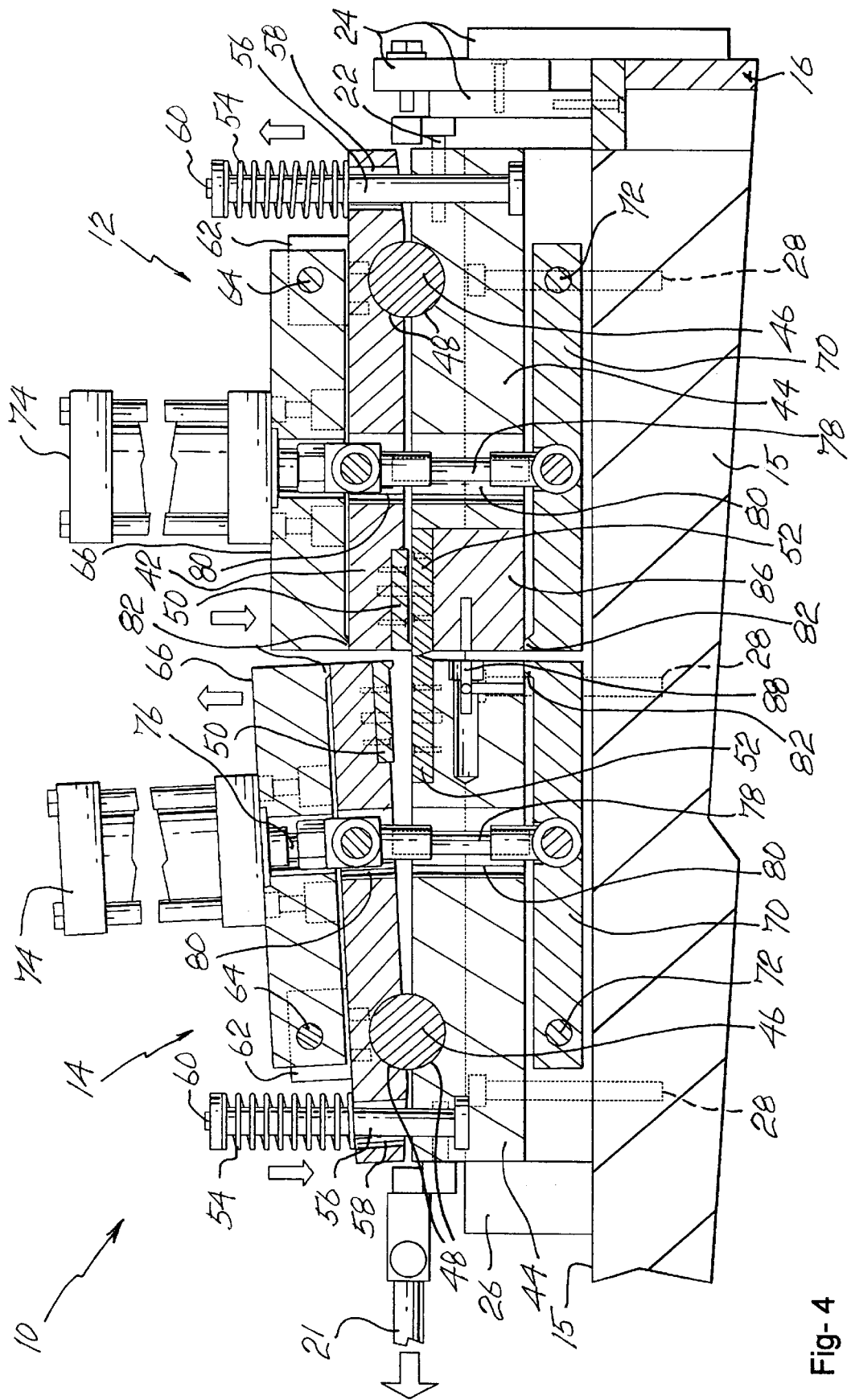
FIG. 4 is a cross-sectional view taken along line 4—4 of FIG. 3, illustrating two clamping jaw assemblies, one being in an open position thereof for receiving a sheet material to be tested while the other is shown in a clamped position thereof to grip the sheet of material to be tested.

Having established the relationship of the stationary and moveable clamping jaw assemblies 12 and 14 of the present invention with respect to peripheral features associated therewith, there will now be described the construction and operation of the clamping jaw assembly of the present invention. Referring now to FIG. 4, it can be seen that the stationary and moveable clamping jaw assemblies 12 and 14 are essentially similar. The stationary and moveable clamping jaw assemblies 12 and 14 are both provided with first and second jaw members 42 and 44. The first jaw member 42 is adapted to pivot on a pin 46 disposed within semi-circular transverse slots 48 which are defined in the first and second jaw members 42 and 44, respectively. Therefore, the first jaw member 42 can move to and from the second jaw member 44, as will be described later. Each first jaw member 42 mounts hardened jaw bit insert 50 while each second jaw member 44 mounts hardened jaw bit insert 52. The jaw bit inserts 50 and 52 form the clamping surfaces of the first and second jaw members 42 and 44, respectively.

A biasing means in the form of a spring 54 mounted on a rod 56 which extends through a hole 58 defined in the first jaw member 42 and which is secured at the lower end thereof to the second jaw member 44 is disposed adjacent the pin 46 of each clamping jaw assembly. The rod 56 is provided at the upper end thereof with a nut 60 to urge the spring 54 against the upper side of the first jaw member 42. Therefore, the spring 54 will hold the clamping surface of the first jaw member 42 in a position away from the clamping surface of the second jaw member 44 such that, when the clamping surface of the first jaw member 42 is moved against the clamping surface of the second jaw member 44, the spring 54 is under compression.

As shown in FIGS. 4 and 5, hinge pads 62 extend upwardly on either side of each first jaw member 42 to receive the ends of a hinge rod 64 which extend through a first load bar 66 for pivotally mounting the same to the corresponding first jaw member 42. As best seen in FIG. 4, the pivot axis of the first and second jaw members 42 and 44 in a clamped position thereof, i.e., the position where the clamping surface of the first jaw member 42 is in contact with the clamping surface of the second jaw member 44, is perfectly aligned along a vertical plan with the pivot axis of the first load bar 66. Referring to FIG. 5, each second jaw member 44 is provided with a cavity 68 at the bottom thereof for accommodating a second load bar 70. The second load bars 70 are pivotally mounted to the second jaw members by means of a hinge rod 72. As for the first load bars 66, the pivot axis of the second load bars 70 is perfectly aligned along a vertical plan with the pivot axis of the first and second jaw members 42 and 44.

A fluid operated cylinder 74, such as an air cylinder, is mounted on each first load bar 66 for closing the first and second jaw members 42 and 44 in a clamped position thereof. More particularly, the piston rod 76 of each fluid operated cylinder 74 is pivotally connected to a rod 78 which extends and moves within a passage 80 defined in the first and second jaw members 42 and 44 and which is in turn pivotally connected to the second load bar 70 such that, when activated, the fluid operated cylinder 74 will act to pull the first and second load bars 66 and 70 together, thereby causing the pivotal movement of the first jaw member 42 towards the second jaw member 44 so as to close the first and second jaw members 42 and 44 in the clamped position thereof. This pivotal movement induces a compression load in the spring 54 which, when the clamping pressure is released, will cause the first and second jaw members 42 and 44 to open up and release the sheet material being tested. It is pointed out that the connection existing between the fluid operated cylinders 74 and the second load bars 70 allows the radial displacement caused by the pivotal movement of the first jaw member 42.

As best seen in FIG. 4, the first and second load bars 66 and 70 are provided at one end thereof with respective load application portions 82 for transferring the load developed by the fluid operated cylinder 74 into direct compression forces at the clamping surfaces of the first and second jaw members 42 and 44. When the first and second jaw members 42 and 44 are closed in the clamped position thereof, the load application portions 82 of the first and second load bars 66 and 70 are perpendicular to both clamping surfaces, i.e., the jaw bit inserts 50 and 52, and positioned along an axis which passes through the meeting point of the clamping surfaces. Therefore, the load developed by the fluid operated cylinders 74 is converted to vertical compression forces between the first and the second load bars 66 and 70 along a vertiCal axis which passes through the center of the pins 46 and along the vertical axis which passes through the load application portions 82 and the clamping surfaces of the first and second jaw members 42 and 44. In other words, the first and second load bars 66 and 70 each act as a load concentrating means to thus ensure that no bending forces or shear stress are induced in either the first or second jaw members 42 and 44.

As shown in FIG. 6, two support plates 84 extend on either side of the jaw bit insert 52 of the moveable clamping jaw assembly 14 for supporting the top target (not shown) of the up-down position sensors (not shown). The two support plates 84 and the jaw bit insert 52 of the moveable jaw assembly 14 define a space which is adapted to accommodate the jaw bit insert 52 of the stationary clamping jaw assembly 12. As best seen in FIG. 4, a cartridge 86 is provided under the jaw bit insert 52 of the stationary clamping jaw assembly 12 for holding the up-down position sensor (not shown) and a zero span sensor (not shown) which is adapted to detect the position of a zero span target 88 located under the jaw bit insert 52 of the moveable clamping jaw assembly 14. Other suitable means could also be provided for recording the tensile force required to overcome the tensile strength of the sheet material. Furthermore, a control panel could be provided for operating the clamping jaw assemblies.

It is pointed out that, although the base plate 15, the side plate 26, and the alignment pads 30 as herein described are respectively made of granite and Teflon materials, it is conceivable that other frictionless material may be provided. It is also noted that the motion of the moveable clamping jaw assembly 14 is constrained only by the friction forces exerted by the above sliding contact surfaces. A pressure transducer monitored by a computer may be provided to determine the pressure in the fluid operated cylinder 18 when the tested sheet material is finally torn. Therefore, the tensile strength of the sheet material can be determined by using an equation, such as tensile strength =(pressure−zero pressure) * calibration constant, where the zero pressure is the pressure required to overcome the friction force exerted by the sliding contact surfaces.

I claim:

1. In a testing apparatus for measuring the tensile strength of a flat sheet of material wherein the flat sheet is clamped at separate locations and tensile force is applied to the flat sheet comprising pairs of clamping jaw assemblies, each such clamping jaw assembly including first and second jaw members having respective clamping surfaces adapted to receive and clamp the flat sheet of material at adjacent points of contact, pressure means to apply a load for closing said first and second jaw members in a clamped position, load concentrating means associated with said pressure means, said load concentrating means being in contact with at least one of said first and second jaw members at a location which is intersected by an axis which is perpendicular to the clamping surfaces in said clamped position and which passes through said clamping surfaces at the points of contact with said flat sheet for transferring the load to said first and second jaw members along said axis, said load concentrating means including first and second load bars which are respectively disposed on a surface of said first and second jaw members opposite to said clamping surfaces thereof, said first and second load bars being provided with respective load application portion which respectively protrude from said first and second load bars towards said first and second jaw members at said locations for transferring the load developed by said pressure means to said first and second jaw members into direct compression forces at said clamping surfaces.

2. A testing apparatus as defined in claim 1, wherein each said clamping jaw assembly includes biasing means for urging said first jaw member to an open position when the load exerted by said pressure means is released.

3. A testing apparatus as defined in claim 2, wherein said first jaw member is pivotally mounted to said second jaw member, and wherein said biasing means comprises a spring mounted on a rod which extends through a hole defined in said first jaw member, said rod being secured at one end thereof to said second jaw member and provided at opposite ends thereof with nut means to hold said spring against said upper jaw member such that, when said upper jaw member is moved against said lower jaw member, said spring is under compression.

4. A testing apparatus as defined in claim 1, wherein each said clamping jaw assembly includes pivot means disposed between said first and second jaw members for directing the motion of said first jaw member relative to said second jaw member, and wherein said load concentrating means are in contact with at least one of said first and second jaw members at a second location which is intersected by an axis parallel to said axis passing through said clamping surfaces in said clamped position and which passes through a center point of said pivot means for transferring the load to said first and second jaw members into direct compression forces at said clamping surfaces, thereby preventing deflections from effecting the uniformity of said clamping surfaces.

5. A testing apparatus as defined in claim 4, wherein said pivot means is a pin having a circular cross-section and extending within semi-circular transverse slots defined in said first and second jaw members, respectively.

6. A testing apparatus as defined in claim 1, wherein said pressure means is a fluid operated cylinder mounted on said first load bar, said cylinder having a piston rod which is adapted to extend and move within a passage defined in said first load bar and in said first and second jaw members, said piston rod being fixed to said second load bar at one end thereof such that, when activated, said cylinder will act to pull said first and second load bars together, thereby closing said first and second jaw members in said clamped position thereof.

7. A testing apparatus as defined in claim 4, wherein said first and second load bars are respectively pivotally mounted at said second location.

8. A testing apparatus as defined in claim 7, wherein said second load bar is pivotally mounted within a cavity defined in said second jaw member.

9. An apparatus for testing the tensile strength of fibers in a flat sheet comprising a base structure, a stationary clamping jaw assembly mounted to said base structure and adapted to clamp a sheet of material to be tested, a moveable clamping jaw assembly mounted to said base structure opposite to said stationary clamping jaw assembly for clamping said sheet material adjacent to said stationary clamping jaw assembly, said moveable clamping jaw assembly being displaceable along a longitudinal axis passing through the center of said stationary clamping jaw assembly;

each said stationary and moveable clamping jaw assemblies including first and second jaw members, said first and second jaw members having respective clamping surfaces to receive and clamp said sheet of material at adjacent points of contact, pressure means to apply a load for closing said first and second jaw members in a clamped position, load concentrating means associated with said pressure means, said load concentrating means being in contact with at least one of said first and second jaw members at a location which is intersected by an axis which is perpendicular to the clamping surfaces in said clamped position and which passes through said clamping surfaces at the points of contact with said flat sheet of paper for transferring the load to said first and second jaw members along said axis, said load concentrating means including first and second load bars which are respectively disposed on a surface of said first and second jaw members opposite to said clamping surfaces thereof, said first and second load bars being provided with respective load application portion which respectively protrude from said first and second load bars towards said first and second jaw members at said locations for transferring the load developed by said pressure means to said first and second jaw members into direct compression forces at said clamping surfaces;

motive means for moving said moveable clamping jaw assembly along said longitudinal axis towards and away from said stationary clamping jaw assembly, said motive means being connected to said moveable clamping jaw assembly so as to apply a force along said clamped surfaces of said first and second jaw members in said clamped position thereof, thereby exerting a tensile force in the sheet of material clamped by said moveable and stationary clamping jaw assemblies.

10. A testing apparatus as defined in claim 9, wherein said stationary clamping jaw assembly is secured to said base structure by way of a bracket means, said bracket means being adapted to provide a reaction force which has the same magnitude and line of action as the force applied by said motive means.

11. A testing apparatus as defined in claim 9, wherein there is provided alignment means to ensure that the moveable clamping jaw assembly is aligned with said stationary clamping jaw assembly.

12. A testing apparatus as defined in claim 11, wherein said alignment means is provided on each side of said stationary and moveable clamping jaw assemblies, said alignment means including a side plate fixedly mounted to said base structure, a pair of alignment pads disposed on opposite sides of said stationary and moveable clamping jaw assemblies, each said alignment pad being connected to a pair of fluid operated cylinders to press said stationary and moveable clamping jaw assemblies against said side plate, said side plate and said alignment pads being made of frictionless material.

13. A testing apparatus as defined in claim 12, wherein said side plate is made of granite material and said side pads are faced with Teflon.

14. A testing apparatus as defined in claim 9, wherein each said stationary and moveable clamping jaw assembly includes biasing means for urging said first jaw member thereof to an open position when the load exerted by said pressure means is released.

15. A testing apparatus as defined in claim 14, wherein said first jaw member is pivotally mounted to said second jaw member, and wherein said biasing means comprises a spring mounted on a rod which extends through a hole defined in said first jaw member, said rod being secured at one end thereof to said second jaw member and provided at opposite ends thereof with nut means to hold said spring against said first jaw member such that, when said first jaw member is moved against said second jaw member, said spring is under compression.

16. A testing apparatus as defined in claim 9, wherein each said stationary and moveable clamping jaw assembly includes pivot means disposed between said first and second jaw members thereof for directing the motion of said first jaw members relative to said second jaw members, and wherein said load concentrating means are in contact with at least one of said first and second jaw members at a second location which is intersected by an axis which is perpendicular to said clamping surfaces in said clamped position and which passes through a center point of said pivot means for transferring the load to said first and second jaw members into direct compression forces, thereby preventing deflections from effecting the uniformity of said clamping surfaces.

17. A testing apparatus as defined in claim 16, wherein said pivot means is a pin having a circular cross-section and extending within semi-circular transverse slots defined in said first and second jaw members, respectively.

18. A testing apparatus as defined in claim 16, wherein said first and second load bars are respectively pivotally mounted at said second location to said first and second jaw members.

19. A testing apparatus as defined in claim 18, wherein said pressure means is a fluid operated cylinder mounted on said first load bar, said cylinder having a piston rod which is adapted to extend and move within a passage defined in said first load bar and in said first and second jaw members, said piston rod being pivotally connected to a rod which is in turn pivotally connected to said second load bar such that, when activated, said cylinder will act to pull said first and second load bars together, thereby causing the pivotal movement of said first jaw member towards said second jaw member so as to close said first and second jaw members in said clamped position thereof.

20. A testing apparatus as defined in claim 19, wherein said second load bar is pivotally mounted within a cavity defined in said second jaw member.

\* \* \* \* \*